US006251625B1

(12) United States Patent
Bommarius et al.

(10) Patent No.: US 6,251,625 B1
(45) Date of Patent: Jun. 26, 2001

(54) PROCESS FOR PREPARING PEPTIDES AND N-CARBAMOYL-PROTECTED PEPTIDES

(75) Inventors: Andreas Bommarius, Frankfurt; Karlheinz Drauz, Freigericht; Uwe Eichhorn, Grosserkammsdorf; Hans-Dieter Jakubke, Leipzig; Matthias Kottenhahn, Freigericht, all of (DE)

(73) Assignee: Degussa Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/011,859

(22) PCT Filed: Jun. 26, 1996

(86) PCT No.: PCT/EP96/02782

§ 371 Date: Apr. 30, 1998

§ 102(e) Date: Apr. 30, 1998

(87) PCT Pub. No.: WO97/03091

PCT Pub. Date: Jan. 30, 1997

(30) Foreign Application Priority Data

| | | |
|---|---|---|
| Jul. 11, 1995 | (DE) | 195 24 710 |
| Feb. 5, 1996 | (DE) | 196 03 844 |
| Feb. 26, 1996 | (DE) | 196 07 100 |

(51) Int. Cl.[7] ............................ C12P 21/06; C07K 16/00

(52) U.S. Cl. ......................... 435/68.1; 435/129; 435/136; 435/171; 435/71.1; 435/71.2; 435/195; 435/227; 530/300; 530/302; 530/331; 530/330; 530/329; 530/328; 530/335; 530/337; 530/343; 530/345; 564/255; 560/345

(58) Field of Search ............................. 435/19, 136, 171, 435/71.1, 71.2, 195, 227, 68.1; 530/300, 302, 331, 330, 329, 328, 335, 337, 343, 345; 564/255; 560/345

(56) References Cited

U.S. PATENT DOCUMENTS

| | | | | |
|---|---|---|---|---|
| 5,350,681 | * | 9/1994 | Iacobucci et al. | 435/68.1 |
| 5,516,660 | * | 5/1996 | Wagner et al. | 435/106 |
| 5,714,355 | * | 2/1998 | Wagner et al. | 435/106 |

* cited by examiner

*Primary Examiner*—Francisco Prats
(74) *Attorney, Agent, or Firm*—Selitto, Behr & Kim

(57) ABSTRACT

The invention concerns a process for the enzymatic preparation of protected di- and oligopeptides and the separation of the protective groups used. The process according to the invention enables peptides to be synthesized simply and economically and the protective group to be separated carefully. The process comprises three reaction steps: 1. Preparation of N-carbamoyl amino acid or N-carbamoyl amino acid derivatives; 2. Formation of the peptide bond between the carbamoyl-protected electrophile and nucelophile; and 3. Separation of the carbamoyl-protective group.

19 Claims, No Drawings

PROCESS FOR PREPARING PEPTIDES AND N-CARBAMOYL-PROTECTED PEPTIDES

The invention relates to a process for the enzymatic preparation of protected di- or oligopeptides and removal of the protective group used by splitting off.

Synthetic short-chain peptides are increasingly used in pharmacology and in parenteral feeding. Kyotorphin (L-Tyr-L-Arg), which promotes the release of enkephalins, that is to say endogenous substances which have an analgesic and tranquillizing action in the brain (Hughes, 1975), may be mentioned as an example of a pharmacologically active dipeptide.

The enzymatic preparation of di- or oligopeptides is already known and generally makes use of protective group technology. The use of a formyl protective group is thus described in U.S. Pat. No. 571,037, that of an acetyl protective group in JP 62074296, that of a benzyl protective group in U.S. Pat. No. 4,935,355 or that of a phenacetyl protective group in Tetrahedron 1992, 48, 1115. These variants have the disadvantage that the protective groups in some cases are not inexpensive (benzyl, phenacetyl), can be split off again only with difficulty (acetyl, formyl) or can be removed (benzyl) only under quite specific conditions (hydrogenolysis).

The object of the invention was therefore to develop a process for the synthesis of peptides which is particularly simple and inexpensive, allows simple and gentle removal of the protective group by splitting off, and allows simple working up and separating-off of the enzyme.

This object of the invention for the preparation of a peptide of the general formula I

I

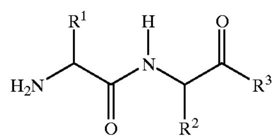

wherein $R^1$ and $R^2$ independently of one another denote hydrogen, $(C_1–C_6)$ alkyl, which can optionally be interrupted or substituted by heteroatoms, such as N, O or S, one [sic] or several times, it being possible for the heteroatoms in their turn to be substituted by hydrogen, $(C_1–C_4)$ alkyl or benzyl or to be bonded to the alkyl group via a double bond, phenyl or benzyl, both of which can optionally be substituted by halogen or hydroxyl once or several times, heteroaralkyl, such as 3-indolylmethyl, 2-, 3- or 4-pyridylmethyl, $R^3$ denotes $(C_1–C_4)$ alkoxy, $NH_2$, hydroxyl, $NR^1R^2$, benzyloxy, which can optionally be substituted by halogen, nitro, $NH_2$, $(C_1–C_4)$ alkyl, $(C_1–C_4)$ alkoxy once or several times, or one or more units of the type II

II

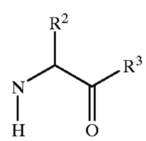

is achieved by a process in which compounds of the type III or a salt form thereof,

III

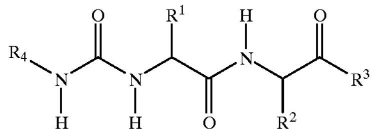

wherein $R^1$, $R^2$ and $R^3$ have the abovementioned meaning and $R^4$ denotes hydrogen, $(C_1–C_4)$ alkyl, phenyl, which can optionally be substituted by halogen, $(C_1–C_4)$ alkyl, $(C_1–C_4)$ alkoxy, nitro, CN, $CF_3$, $(C_1–C_6)$ alkoxycarbonyl, COOH or —$NR^1R^2$ once or several times, aralkyl, such as benzyl, which can be substituted in its turn by halogen, $(C_1–C_4)$ alkyl or $(C_1–C_4)$ alkoxy, naphthyl, heteroaralkyl, such as 2-, 3- or 4-thienyl, 2-, 3- or 4-pyridyl or 2-quinolyl are reacted with a carbamoylase, optionally in the presence of a solvent, or the carbamoyl protective group is split off chemically, optionally in the presence of a solvent and optionally in the presence of an acid.

It has furthermore been found that carbamoyl-protected peptides of the general structure III,

III

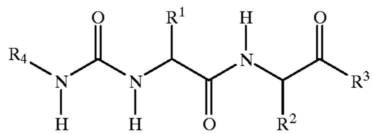

wherein $R^1$ and $R^2$ independently of one another denote hydrogen, $(C_1–C_6)$ alkyl, which can optionally be interrupted or substituted by heteroatoms, such as N, O or S, one [sic] or several times, it being possible for the heteroatoms in their turn to be substituted by hydrogen, $(C_1–C_4)$ alkyl or benzyl or to be bonded to the alkyl group via a double bond, phenyl or benzyl, both of which can optionally be substituted by halogen or hydroxyl once or several times, heteroaralkyl, such as 3-indolylmethyl, 2-, 3- or 4-pyridylmethyl, $R^3$ denotes $(C_1–C_4)$ alkoxy, $NH_2$, hydroxyl, $NR^1R^2$, benzyloxy, which can optionally be substituted by halogen, nitro, $NH_2$, $(C_1–C_4)$ alkyl, $(C_1–C_4)$ alkoxy once or several times, $R^4$ denotes hydrogen, $(C_1–C_4)$ alkyl, phenyl, which can optionally be substituted by halogen, $(C_1–C_4)$ alkyl, $(C_1–C_4)$ alkoxy, nitro, CN, $CF_3$, $(C_1–C_6)$ alkoxycarbonyl, COOH or —$NR^1R^2$ once or several times, aralkyl, such as benzyl, which car be substituted in its turn by halogen, $(C_1–C_4)$ alkyl or $(C_1–C_4)$ alkoxy, naphthyl, heteroaralkyl, such as 2-, 3- or 4-thienyl, 2-, 3- or 4-pyridyl or 2-quinolyl are obtained by a process in which a compound of the type IV or a salt form of IV, in which $R^1$ and $R^4$ have the abovementioned meaning,

IV

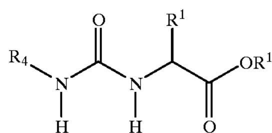

is reacted with a compound of the type V, or of [sic] an acid addition salt thereof, wherein $R^2$ and $R^3$ have the above-mentioned meaning,

V

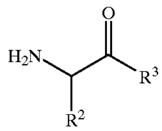

optionally in the presence of a solvent and optionally in the presence of a base.

The term "alkyl groups" is to be understood as meaning both "straight-chain" and "branched" alkyl groups.

The term "straight-chain alkyl group" is to be understood as meaning, for example, radicals such as methyl, ethyl, n-propyl, n-butyl, n-pentyl, n-hexyl, and the term "branched alkyl group" is to be understood as meaning radicals such as, for example, isopropyl or tert.-butyl.

The term halogen represents fluorine, chlorine, bromine or iodine. The term "alkoxy group" represents radicals such as, for example, methoxy, ethoxy, propoxy, butoxy, isopropoxy, isobutoxy or pentoxy.

Dipeptides, such as, for example, aspartam, can preferably be prepared by this process.

Another advantage of the process is that the peptide coupling can be carried out in a highly dense suspension, it being possible for the substrate and product to be present in partial [sic] solid form.

The novel process for the synthesis of peptides using, as the intermediate product, the carbamoyl-protected peptides described comprises three reaction steps.

A) Preparation of the N-carbamoyl-amino acid or of the N-carbamoyl-amino acid derivative B) Linking of the peptide bond between the carbamoyl-protected electrophile and the nucleophile C) Removal of the carbamoyl protective group by splitting off The preparation of the N-carbamoyl-amino acid or of the N-carbamoyl-amino acid derivative can be carried out in a manner known per se from the literature. Preferably, the reaction of the amino acid or of the amino acid derivative with an isocyanate of the general structure VI, $$R^1\text{—NCO} \qquad \text{VI}$$

wherein $R^1$ has the meaning given above, in a two-phase system of $H_2O$/organic solvent, it being possible for the organic solvent to be, for example, toluene, chlorobenzene or tert.butyl methyl ether, is carried out. The reaction is carried out at temperatures between 0° C. and 120° C., preferably between 20° C. and 70° C. If appropriate, an inorganic base, such as, for example, NaOH, KOH, $K_2CO_3$, $Na_2CO_3$, potassium bicarbonate or sodium bicarbonate, or an organic base, such as, for example, triethylamine or tributylamine, can be added to the reaction mixture. The phenyl isocyanate of the structure III is advantageously used in a slight excess.

Reactions to give the N-carbamoyl-protected amino acids or amino acid derivatives with a cyanate of the structure VII, $$M^{\ominus\ominus}OCN \qquad \text{VII}$$

wherein $M^{\oplus}$ represents $Na^{\oplus}$, $K^{\oplus}$, $Ag^{\oplus}$, $Pb^{\oplus}$ (OCN) or ammonium ions, such as, for example, tetraethylammonium, tetrabutylammonium or benzyltriethylammonium, are particularly preferred.

The reaction is carried out in a manner known per se in aqueous solution at temperatures between 0° C.–120° C., preferably between 60° C.–100° C., and if appropriate with the addition of an inorganic base, such as, for example, NaOH, KOH, $K_2CO_3$ or $Na_2CO_3$. It has proved favourable if the reaction is carried out in the presence of slight excesses of 1.01–2 equivalents, preferably 1.1–1.2 equivalents, of cyanate.

The linking of the peptide bond is carried out in a manner known per se with the aid of a hydrolase (Jakubke, Kuhl and Könnecke; Angew. Chem. 1985, vol. 97, p.p. 79–87). It is irrelevant for the reaction conditions here whether the peptide linking proceeds under kinetic or thermodynamic control. The process according to the invention can be applied to both process variants. The term "salt form" of the compound type IV is to be understood generally as meaning ionic structures. Thus, a possible cation, such as, for example, $Na^{\oplus}$, $K^{\oplus}$, $Ag^{\oplus}$, $Pb^{2\oplus}$ or an ammonium ion, such as, for example, tetraethylammonium, tetrabutylammonium or benzyltriethylammonium, can neutralize a negative charge on the compound type IV. The negative charge here can be distributed over the molecule (compound type IV) or localized on a nitrogen atom or the carboxyl group in the form of a carboxylate group.

Suprisingly, this reaction with the carbamoyl group, which is novel for this reaction sequence, as the protective group proceeds in good space/time yields and allows easy isolation of the products. The broad applicability of the reaction is also surprising.

An acid addition salt of V is to be understood as meaning, for example, an HCl salt, HBr salt or an $H_2SO_4$ salt.

The carbamoyl protective group is split off, for example, under mild reaction conditions with the aid of a carbamoylase. This type of removal of carbamoyl groups from peptides by splitting off is novel. It is particularly advantageous because, in addition to the enzyme, it requires only water as a substance used for the cleavage and because, in addition to the peptide, only carbon dioxide and ammonia are formed as cleavage products, from which the peptide can be separated off very easily. The carbamoylase can be employed for this reaction optionally in the partly purified, purified, isolated or immobilized state. The reaction is irreversible, and up to 100% conversion are [sic] observed. The reaction is carried out in aqueous solution at temperatures between 10–50° C., preferably 20–35° C., especially preferably 25–30° C., and pH values between 5 and 11, preferably 6.5–8.5, and especially preferably between 7–8.

Carbon dioxide and ammonia, which optionally escape from the reaction mixture by gassing out, are formed during the hydrolysis with carbamoylase.

From the peptide solution treated with carbamoylase, the now unprotected peptide can be precipitated out and isolated by crystallization by means of evaporation, cooling or, if appropriate, addition of organic solvents.

Carbamoylases which are deposited at the Deutsche Sammlung für Mikroorganismen [German Collection of Microorganisms] under the following numbers have proved suitable: DSM 7329, DSM 7330, DSM 9771. However, the novel process does not exclude microorganisms other than those mentioned above.

The removal of the carbamoyl protective group by splitting off can also be carried out analogously to that described above in the presence of an additional enzyme (in addition to the carbamoylases mentioned), such as, for example, thermolysin.

The carbamoyl protective group can also be split off chemically. This type of removal of carbamoyl groups from peptides by splitting off is likewise novel. The removal by splitting off can in principle be carried out with any $NO^{\oplus}$ donor. $NaNO_2$ or $NO^{\oplus}BF_4^{\ominus}$ are particularly suitable. The reaction is optionally carried out in an aqueous medium and/or an inert organic solvent, such as an aromatic hydrocarbon, such as, for example, toluene or chlorobenzene, in an aliphatic hydrocarbon, a halogenated hydrocarbon, such as, for example, methylene chloride, or an ether, such as, for example, methyl tert.butyl ether or tetrahydrofuran. Depending on the $NO^{\oplus}$ donor, the reaction is carried out in the presence of an acid, such as, for example, HCl or $H_2SO_4$. Particularly suitable reaction temperatures are temperatures between +120° C. and −30° C., particularly preferably +60° C. and −20° C., especially preferably +25° C. and 0° C. If an acid is added, the pH should be between −0.5 and 5, preferably 0 and 2. The reaction is advantageous since, in addition to nitrogen, $CO_2$ and, where appropriate, a salt, it produces no other by-products at all and the conversion proceeds with high yields and the desired formation of product without cleavage products. Another advantage of the reaction is the easy working up.

The novel process is explained in more detail with the aid of the following embodiment examples, but is not limited to these.

EXAMPLE 1

Example of the Preparation of N-carbamoyl-amino Acids and Derivatives Using the Example of N-carbamoyl-L-aspartic Acid 12 g (0.3 mol) NaOH lozenges are initially introduced into approx. 200 ml $H_2O$ and are dissolved. Aspartic acid (33.3 g, 0.25 mol) is added as a solution in 50 ml water and the reaction mixture is heated to 80° C. The pH is 8.7. 16.6 g (0.255 mol) sodium cyanate are added in the course of 5 min (pH rises to 9.3, T to 86° C.). After a reaction time of 1 h, aspartic acid is no longer detectable.

Examples of the Synthesis of the Peptides

The amino acids and peptides are abbreviated according to the internationally applicable rules (IUPAC-JUB Joint Commission on Biochemical Nomenclature (JCBN); Nomenclature and Symbolism for Amino Acids and Peptides. Eur. J. Biochem. 158, 9–37 (1984)).

AC-: aminocarbonyl- (carbamoyl-, $NH_2CO$—)

EXAMPLE 2

Synthesis of AC-Asp-Phe-OMe

80 μl buffer (0.5 M Hepes/$Na^+$; pH 7) are added to 50 mg (0.2 mmol) AC-Asp(OK)-OK and 83 mg (0.4 mmol) H-Phe-OME.HCl in a closable polypropylene vessel and the components are immediately mixed intensively with a spatula. The reaction mixture is thermostatically controlled at 40° C. on a water-bath and the reaction is then started with 20 μl buffer comprising 4 mg thermolysin preparation (Sigma P 1512).

After 1 h, 2.5 h, 16 h, 22 h, 29 h and 39 h, samples are taken and the reaction is stopped in 0.75 ml 4% aqueous acetic acid. The analytical evaluation is carried out here, as in the following examples, by means of HPLC and comparisons with an authentic sample.

| | Yield: | |
|---|---|---|
| Time (h) | Yield (% of th.) | H-Phe-OH/H-Phe-OMe (t = 0) (−/−) |
| 1 | 7 | 0.023 |
| 2.5 | 14 | 0.030 |
| 16 | 55 | 0.083 |
| 22 | 69 | 0.119 |
| 29 | 77 | 0.12 |
| 39 | 81 | 0.125 |

EXAMPLES 3a–e

Analogously to example 2, instead of 80 μl buffer, 120 (a), 160 (b), 200 (c), 240 (d) and 280 μl buffer are used to suspend the reactants. Sampling is carried out after 29 and 39 h.

| | | Yield: | | |
|---|---|---|---|---|
| | Yield (% of th.) | | H-Phe-OH/H-PHe-OMe (t = 0) (−/−) | |
| Example | 29 h | 39 h | 29 h | 39 h |
| 3a | 79 | 82 | 0.139 | 0.136 |
| 3b | 79 | 76 | 0.144 | 0.165 |
| 3c | 73 | 75 | 0.169 | 0.169 |
| 3d | 64 | 64 | 0.216 | 0.22 |
| 3e | 59 | 61 | 0.215 | 0.224 |

EXAMPLE 4

80 μl buffer (0.5 M Hepes/$Na^+$; pH 7) are added to 44 mg (0.175 mmol) AC-Asp(OK)-OK and 41.5 mg (0.2 mmol) H-Phe-OMe.HCl in a closable polypropylene vessel and the components are immediately suspended intensively with a spatula. After transfer of the reaction vessel into a water-bath thermostatically controlled at 40° C., the reaction is started by addition of 15 μl buffer comprising 1.5 mg thermolysin preparation (Sigma P 1512). After 1 h, 2.5 h, 5 h, 6.5 h and 22 h, samples are taken and the reaction is stopped in 0.75 ml 4% aqueous acetic acid and the product is analysed by means of HPLC.

| | Yield: | |
|---|---|---|
| Time (h) | Yield (% of th.) | H-Phe-OH/H-Phe-OMe (t = 0) (−/−) |
| 1 | 7 | 0.023 |
| 2.5 | 16 | 0.039 |
| 5 | 23 | 0.064 |
| 6.5 | 28 | 0.078 |
| 22 | 48 | 0.136 |

EXAMPLE 5

Analogously to example 4, instead of 80 μl buffer, 10 (a), 30 (b), 50 (c), 130 (d) and 180 μl (e) buffer are added to the reactants. Sampling is carried out after 22 h.

| Yield: | | |
|---|---|---|
| Example | Yield (% of th.) | H-Phe-OH/H-Phe-OMe (t = 0) (–/–) |
| 5a | 7 | 0.034 |
| 5b | 31 | 0.072 |
| 5c | 29 | 0.105 |
| 5d | 39 | 0.319 |
| 5e | 41 | 0.249 |

EXAMPLE 6

Synthesis of AC—Asp—Phe—$NH_2$

400 μl buffer (0.5 M Hepes/$Na^+$; ph [sic] 7) are added to 250 mg (1.0 mmol) AC-Asp(OK)-OK and 400 mg (2.0 mmol) H—Phe—$NH_2$.HCl in a closable polypropylene vessel and the components are immediately suspended intensively with a spatula. After transfer of the reaction vessel into a water-bath thermostatically controlled at 40° C., the reaction is started by addition of 50 μl buffer comprising 10 mg thermolysin preparation (Sigma P 1512). After 44 h, samples are taken and the reaction is stopped in 0.75 ml 4% aqueous acetic acid and the product is analysed by means of HPLC. The reaction is ended by addition of 1 ml 1 N aqueous HCl and left overnight at 4° C. The precipitate is then filtered off with suction and washed with ice-cold water.

Yield: 62% of th. Melting range: 221–223° C. $^1$H-NMR ($D_6$-DMSO, 300 MHz); δ=2.38–2.6 (m, 2 H, —$^{\beta}CH_2$—), δ=2.8–2.88 (m, 1 H, —$^{\beta}CH_2$—), δ=5.72 (s, 2 H, —$NH_2$), δ=6.30 (d, 1 H, —$^{\alpha}$NH—, J=7.69), δ=7.13 (s, 1 H, Phe—$NH_2$), δ=7.26– 7.28 (m, 5 H, Phe—$C_6H_5$), δ=7.33 (s, 1 H, Phe—$NH_2$), δ=7.83 (d, 1 H, —$^{\alpha}$NH—, J=8.4)

EXAMPLE 7

Synthesis of AC—Asp—Phe—Leu—$NH_2$ 67.4 mg (0.2 mmol) AC—Asp—Phe—OMe and 26 mg (0.2 mmol) H—Leu—$NH_2$ (Bachem Biochemica GmbH) are dissolved in 180 μl buffer (0.5 M Hepes/$Na^+$, pH 7.9) in a polypropylene reaction vessel. After addition of 10 μl 10 M aqueous NaOH, the reaction is started with 10 μl α-chymotrypsin solution (10 mg/ml buffer; Serva, 3×cryst.). After 2, 5, 10, 20, 30 and 60 min, samples are taken, dissolved in 1 ml 4% aqueous acetic acid and analysed by means of HPLC. The reaction mixture which remains is taken up in 1 ml methanol, filtered and 1 ml 1 N aqueous HCl and 4 ml water are added to the filtrate. AC—Asp—Phe—Leu—$NH_2$ crystallized [sic] out within 48 h. The crystals were [sic] separated off and washed 2 times with ice-cold water (approx. 1.5 ml each time) and then dried over $P_4O_{10}$ in vacuo.

| Yield: | | |
|---|---|---|
| Time (min) | Ac-Asp-Phe-OH (% of th [sic]) | AC-Asp-Phe-Leu-$NH_2$ (% of th.) |
| 2 | 18.3 | 11.6 |
| 5 | 19 | 23.9 |
| 10 | 19.8 | 41.5 |
| 20 | 21.2 | 60.5 |
| 30 | 21.6 | 70.2 |
| 60 | 20.8 | 79.1 |

$^1$H-NMR; COSY (DMSO, 300 MHz): δ=0.82 (d, 3 H, Leu—$^{\delta}CH_3$), δ=0.87 (d, 3 H, Leu—$^{\delta}CH_3$), δ=1.41–1.6 (m, 3 H, Leu—$^{\gamma}$CH—, Leu—$^{\beta}CH_2$—), δ=2.35–2.58 (m, 2 H, Asp—$^{\beta}CH_2$—), δ=2.81–3.06 (m, 2 H, Phe—$^{\beta}CH_2$—), δ=4.18 (dt, 1 H, Leu—$^{\alpha}$CH—), δ=4.33 (dt, 1 H, Asp—$^{\alpha}$CH—), δ=4.44 (dt, 1 H, Phe—$^{\alpha}$CH—), δ=5.70 (s, 2 H, AC—$NH_2$), δ=6.30 (d, 1 H, Asp—$^{\alpha}$NH—), δ=6.96 (s, 1 H, Leu—$NH_2$), δ=7.05 (s, 1 H, Leu—$NH_2$), δ=7.14–7.27 (m, 5 H, Phe—$C_6H_5$), δ=7.85–7.96 (m, 2 H, Leu—$^{\alpha}$NH, Phe-$^{\alpha}$NH)

EXAMPLE 8

Synthesis of AC—Asp—Phe—Ile—Gly—OMe

Analogously to example 7, instead of H—Leu—$NH_2$, 0.2 mmol (47.8 mg) H—Ile—Gly—OMe.HCl are employed. To establish the pH, 35 μl of the buffer are replaced by 10M aqueous NaOH.

| Yield after 70 min: | | |
|---|---|---|
| AC-Asp-Phe-OH (% of th.) | AC-Asp-Phe-Ile-Gly-OH (% of th.) | AC-Asp-Phe-Ile-Gly-OMe (% of th.) |
| 28.4 | 3.9 | 67.7 |

$^1$H-NMR; COSY(DMSO, 300 MHz): δ=0.77–0.88 (m, 6 H, Ile—$^{\delta}CH_3$), δ=1.00–1.15 (m, 1 H, Ile—$^{\gamma}CH_2$—), δ=1.38–1.52 (m, 1 H, Ile—$^{\gamma}CH_2$—), δ=1.65–1.78 (m, 1 H, Ile—$^{\beta}$CH—), δ=2.34–2.58 (m, 2 H, Asp—$^{\beta}CH_2$—), δ=2.78–2.88 (m, 1 H, Phe—$^{\beta}CH_2$—), δ=2.94–3.2 (m, 1 H, Phe—$^{\beta}CH_2$—), δ=3.62 (s, 3 H, $OCH_3$), δ=3.75–3.95 (m, 2 H, Gly—$^{\alpha}CH_2$—), δ=4.17 (t, 1 H, Ile—$^{\alpha}$CH—), δ=4.30–4.40 (m, 1 H, Asp—$^{\alpha}$CH—), δ=4.48–4.58 (m, 1 H, Phe—$^{\alpha}$CH—), δ=5.7 (s-broad, AC—$NH_2$), δ=6.30 (d, 1 H, Asp—$^{\alpha}$NH—), δ=7.12–7.26 (m, 5 H, Phe—$C_6H_5$—), δ=7.80 (d, 1 H, Phe—$^{\alpha}$NH—), δ=7.92 (d, 1 H, Leu—$^{\alpha}$NH—), δ=8.32 (t, 1 H, Gly—$^{\alpha}$NH—).

EXAMPLE 9

Synthesis of AC—Tyr—Ile—Ala—$NH_2$ a) 45 μl buffer (0.5 M Hepes/$Na^+$; pH 7) are added to 44.8 mg (0.2 mmol) AC—Tyr—OH and 47.4 mg (0.2 mmol) H—Ile—Ala—$NH_2$.HCl in a closable polypropylene vessel and the components are immediately suspended intensively with a spatula. The pH is established by addition of 25 μl 10 M aqueous NaOH. After transfer of the reaction vessel into a water-bath thermostatically controlled at 40° C., the reaction is started by addition of 10 μl buffer comprising 1 mg thermolysin preparation (Sigma P 1512). After 3 h, a sample is taken and the reaction is stopped in 1 ml 4% aqueous acetic acid and 200 μl acetonitrile and the product is analysed by means of HPLC. The reaction mixture which remains is worked up as in example 7, with the difference that instead of 1 N HCl, 4% aqueous acetic acid is used.

Yield of AC—Tyr—Ile—Ala—$NH_2$ after 3 h: 76% of th. $^1$H-NMR;COSY(DMSO), 300 MHz): δ=0.76–0.84 (m, 6 H, Ile—$^{\delta}CH_3$, Ile—$^{\gamma}CH_3$), δ=1.00–1.12 (m, 1 H, Ile—$^{\gamma}CH_2$—), δ=1.22 (d, 3 H, Ala—$^{\beta}CH_3$), δ=1.36–1.42 (m, 1 H, Ile—$^{\gamma}CH_2$—), δ=1.68–1.78 (m, 1 H, Ile—$^{\beta}$CH—), δ=2.56–2.68 (m, 1 H, Tyr—$^{\beta}CH_2$—), δ=2.80–2.90 (m, 1 H, Tyr—$^{\beta}CH_2$—), δ=4.12–4.24 (m, 2 H, Ala—$^{\alpha}$CH—, Ile—$^{\alpha}$CH—), δ=4.28–4.38 (m, 1 H, Tyr—$^{\alpha}$CH—), δ=5.58 (s, 2 H, AC—$NH_2$), δ=6.03 (d, 1 H, Tyr—$^{\alpha}$NH—), δ=6.61 (d, 2 H, Tyr—ArH), δ=6.92–6.98 (m, 3 H, 2 Tyr—ArH, 1 Ala—$NH_2$), δ=7.20 (s, 1 H, Ala—$NH_2$), δ=7.84 (d, 1 H, Ala—$^{\alpha}$NH—), δ=7.92 (d, 1 H, Ile—$^{\alpha}$NH—), δ=9.12 (s, 1 H, Tyr—OH)

b) Analogously to example 9a, 224 mg (1.0 mmol) AC—Tyr—OH, 237.7 mg (1.0 mmol) H—Ile—Ala—$NH_2$.HCl, 225 $\mu$l buffer, 125 $\mu$l 10 M NaOH and 50 $\mu$l thermolysin suspension comprising 5 mg thermolysin (Sigma P1512) are employed.

Yield of AC—Tyr—Ile—Ala—$NH_2$ after 16 h: 228 mg (=56% of th.)

EXAMPLE 10

Synthesis of AC—Tyr—Val—$NH_2$

Analogously to example 9a, instead of H—Ile—Ala—$NH_2$.HCl, 31.2 mg (0.2 mmol) H—Val—$NH_2$.HCl are employed.

Yield of AC—Tyr—Val—$NH_2$ after 18 h: 65% of th. $^1$H-NMR ($D_6$-DMSO, 300 MHz): δ=0.78–0.88 (m, 6 H, Val—$^{\gamma}CH_3$), δ=1.92–2.00 (m, 1 H, Val—$^{\beta}$CH—), δ=2.58–2.68 (m, 1 H, Tyr—$^{\beta}CH_2$—), δ=2.80–2.90 (m, 1 H, Tyr—$^{\beta}CH_2$—), δ=4.11 (dd, 1 H, Val—$^{\alpha}$CH—), δ=4.28–4.38 (m, 1 H, Tyr—$^{\alpha}$CH—), δ=5.57 (s, 2 H, AC—$NH_2$), δ=6.08 (d, 1 H, Tyr—$^{\alpha}$NH—), δ=6.62 (d, 2 H, Tyr—ArH), δ=6.97 (d, 2 H, Tyr—ArH), δ=7.03 (s, 1 H, Val—$NH_2$), δ=7.31 (s, 1 H, Val—$NH_2$), δ=7.67 (d, 1 H, Val—$^{\alpha}$NH—), δ=9.12 (s, 1 H, Tyr—OH)

EXAMPLE 11

Synthesis of AC—Tyr—Met—$NH_2$

Analogously to example 9a, instead of H—Ile—Ala—$NH_2$.HCl, 37 mg (0.2 mmol) H—Met—$NH_2$.HCl are employed.

Yield of AC—Tyr—Met—$NH_2$ after 14 h: 75% of th. $^1$H-NMR ($D_6$-DMSO, 300 MHz); δ=1.75–1.85 (m, 1 H, Met—$^{\beta}CH_2$—), δ-1.88–2.00 (m, 1 H, Met—$^{\beta}CH_2$—), δ=2.02 (s, 3 H, Met—S—$CH_3$), δ=2.30–2.45 (m, 2 H, Met—$^{\beta}CH_2$—), δ=2.60–2.85 (m, 2 H, Tyr—$^{\beta}CH_2$—), δ=4.15–4.28 (m, 2 H, Tyr—$^{\alpha}$CH—, Met—$^{\alpha}$CH—), δ=5.65 (s, 2 H, AC—$NH_2$), δ=6.28 (d, 1 H, Tyr—$^{\alpha}$NH—), δ=6.63 (d, 2 H, Tyr—ArH), δ=6.97 (d, 2 H, Tyr—ArH), δ=7.04 (s, 1 H, Met— $NH_2$), δ=7.25 (s, 1 H, Met—$NH_2$), δ=8.08 (d, 1 H, Met—$^{\alpha}$NH—), δ=8.54 (s, 1 H, Tyr—OH)

EXAMPLE 12

Synthesis of AC—Tyr—Nvl—$NH_2$

Analogously to example 9a, instead of H—Ile—Ala—$NH_2$.HCl, 31.2 mg (0.2 mmol) H—Hvl—$NH_2$.HCl [sic] are employed.

Yield of AC—Tyr—Nvl—$NH_2$ after 14 h: 88% of th. $^1$H-NMR ($D_6$-DMSO, 300 MHz): δ=0.85 (t, 3 H, Nvl—$^{\delta}CH_3$), δ=1.18–1.32 (m, 2 H, Nvl—$^{\gamma}CH_2$—), δ=1.45–1.68 (m, 2 H, Nvl—$^{\beta}CH_2$—), δ=2.55–2.68 (m, 1 H, Tyr—$^{\beta}CH_2$—), δ=2.78–2.88 (m, 1 H, Tyr—$^{\beta}CH_2$—), δ=4.12–4.30 (m, 2 H, Tyr—$^{\alpha}$CH—, Nvl—$^{\alpha}$CH—), δ=5.59 (s, 2 H, AC—$NH_2$), δ=6.02 (d, 1 H, Tyr—$^{\alpha}$NH—), δ=6.62 (d, 2 H. Tyr—ArH), δ=6.94–6.99 (m, 3 H, 2 Tyr—ArH, 1 Nvl—$NH_2$), δ=7.21 (s, 1 H, Nvl—$NH_2$), δ=7.79 (d, 1 H, Met—$^{\alpha}$NH—), δ=9.12 (s, 1 H, Tyr—OH)

EXAMPLE 13

Synthesis of AC—Tyr—Phe—$NH_2$

Analogously to example 9a, instead of H—Ile—Ala—$NH_2$.HCl, 40 mg (0.2 mmol) H—Phe—$NH_2$.HCl are employed.

Yield of AC—Tyr—Phe—$NH_2$ after 1 h: 86% of th. $^1$H-NMR ($D_6$-DMSO, 300 MHz): δ=2.72–2.88 (m, 3 H, —$^{\beta}CH_2$—), δ=1.98–3.06 (m, 1 H, —$^{\beta}CH_2$—), δ=4.12–4.20 (m, 1 H, —$^{\alpha}$CH—), δ=4.38–4.46 (m, 1 H, —$^{\alpha}$CH—), δ=5.59 (s, 2 H, AC—$NH_2$), δ=5.97 (d, 1 H, Tyr—$^{\alpha}$NH—), δ=6.61 (d, 2 H, Tyr—ArH), δ=6.92 (d, 2 H, Tyr—ArH), δ=7.08 (s, 1 H, Phe—$NH_2$), δ=7.15–7.28 (m, 5 H, Phe—$C_6H_5$), δ=7.32 (s, 1 H, Phe—$NH_2$), δ=7.92 (d, 1 H, Phe—$^{\alpha}$NH—), δ=9.12 (s, 1 H, Tyr—OH)

EXAMPLE 14

Synthesis of AC—Tyr—Phe—OMe

Analogously to example 9a, instead of H—Ile—Ala—$NH_2$.HCl, 43 mg (0.2 mmol) H—Phe—OMe.HCl are employed. The amount of thermolysin used is 2 mg.

Yield of AC—Tyr—Phe—OMe after 14 h: 81% of th. $^1$H-NMR ($D_6$-DMSO, 300 MHz): δ=2.50–2.62 (m, 1 H, —$^{\beta}CH_2$—), δ=2.72–2.85 (m, 1 H, —$^{\beta}CH_2$—), δ=2.90–3.08 (m, 2 H, —$^{\beta}CH_2$), δ=3.58 (s, 3 H, —O—$CH_3$), δ=4.25–4.35 (m, 1 H, —$^{\alpha}$CH—), δ=4.44–4.52 (m, 1 H, —$^{\alpha}$CH—), δ=5.52 (s, 2 H, AC—$NH_2$), δ=5.99 (d, 1 H, Tyr—$^{\alpha}$NH—), δ=6.62 (d, 2 H, Tyr—ArH), δ=6.94 (d, 2 H, Tyr—ArH), δ=7.15–7.30 (m, 5 H, Phe—$C_6H_5$), δ=8.36 (d, 1 H, Phe—$^{\alpha}$NH—), δ=9.14 (s, 1 H, Tyr—OH)

EXAMPLE 15

Synthesis of AC—Tyr—Ile—$NH_2$

Analogously to example 9a, instead of H—Ile—Ala—$NH_2$.HCl, 33.2 mg (0.2 mmol) H—Ile—$NH_2$.HCl are employed.

Yield of AC—Tyr—Ile—$NH_2$ after 18 h: 68.9% of th. $^1$H-NMR ($D_6$-DMSO, 300 MHz): δ=0.76–0.86 (m, 6 H, Ile—$^{\beta}CH_3$, Ile—$^{\gamma}CH_3$), δ=0.99–1.12 (m, 1 H, Ile—$^{\gamma}CH_2$—), δ=1.35–1.46 (m, 1 H, Ile—$^{\gamma}CH_2$—), δ=1.62–1.76 (m, 1 H, Ile—$^{\beta}$CH—), δ=2.58–2.68 (m, 1 H, Tyr—$^{\beta}CH_2$—), δ=2.79–2.88 (m, 1 H, Tyr—$^{\beta}CH_2$—), δ=4.12 (dd, 1 H, Ile—$^{\alpha}$CH—), δ=4.26–4.37 (m, 1 H, Tyr—$^{\alpha}$CH—), δ=5.58 (d, 2 H, AC—$NH_2$), δ=6.06 (d, 1 H, Tyr—$^{\alpha}$NH—), δ=6.62 (d, 2 H, Tyr—ArH), δ=6.96 (d, 2 H, Tyr—ArH), δ=7.02 (s, 1 H, Ile— $NH_2$), δ=7.31 (s, 1 H, Ile—$NH_2$), δ=7.68 (d, 1 H, Ile—$^{\alpha}$NH—), δ=9.12 (s, 1 H, Tyr—OH)

EXAMPLE 16

Synthesis of AC—Tyr—Leu—$NH_2$

Analogously to example 9a, 224 mg (1.0 mmol) AC—Tyr—OH, 130 mg (1.0 mmol) H—Leu—$NH_2$ (Bachem Feinchemikalien AG), 225 $\mu$l buffer, no NaOH and 50 $\mu$l thermolysin suspension comprising 5 mg thermolysin (Sigma P1512) are employed.

Yield of AC—Tyr—Leu—$NH_2$ after 16 h: 127.8 mg (=38% of th.) $^1$H-NMR ($D_6$-DMSO, 300 MHz): δ=0.80–0.92 (m, 6 H, Leu—$^{\delta}CH_3$), δ=1.42–1.62 (m, 3 H, Leu—$^{\gamma}$CH—, Leu—$^{\beta}CH_2$—), δ=2.58–2.70 (m, 1 H, Tyr—$^{\beta}CH_2$—), δ=2.79–2.88 (m, 1 H, Tyr—$^{\beta}CH_2$—), δ=4.16–4.30 (m, 2 H, Leu—$^{\alpha}$CH—, Tyr—$^{\alpha}$CH—), δ=5.60 (s, 2 H, AC—$NH_2$), δ=6.02 (d, 1 H, Tyr—$^{\alpha}$NH—), δ=6.63 (d, 2 H, Tyr—ArH), δ=6.93–7.00 (m, 2 H, Tyr—ArH, 1 H, Leu—$NH_2$), δ=7.19 (s, 1 H, Leu—$NH_2$), δ=7.83 (d, 1 H, Leu—$^{\alpha}$NH—), δ=9.15 (s, 1 H, Tyr—OH)

EXAMPLE 17

Synthesis of AC—Tyr—Ile—Gly—OMe

Analogously to example 9a, instead of H—Ile—Ala—$NH_2$.HCl, 47.8 mg (0.2 mmol) H—Ile—Gly—OMe.HCl are employed.

Yield of AC—Tyr—Ile—Gly—OMe after 3 h: 89% of th. $^1$H-NMR;COSY($D_6$-DMSO, 300 MHz): δ=0.76–0.88 (m, 6 H, Ile—$^{\delta}CH_3$, Ile—$^{\gamma}CH_3$), δ=1.00–1.14 (m, 1 H, Ile—$^{\gamma}CH_2$—), δ=1.36–1.52 (m, 1 H, Ile—$^{\gamma}CH_2$—), δ=1.65–1.78 (m, 1 H, Ile—$^{\beta}$CH—), δ=2.55–2.68 (m, 1 H, Tyr—$^{\beta}CH_2$—), δ=2.75–2.86 (m, 1 H, Tyr—$^{\beta}CH_2$—), δ=3.62 (s, 3 H, —O—$CH_3$), δ=3.84 (t, 2 H, Gly—$^{\alpha}CH_2$—), δ=4.27–4.35 (m, 1 H, Ile—$^{\alpha}$CH—), δ=4.38–4.48 (m, 1 H, Tyr—$^{\alpha}$CH—), δ=5.57 (s, 2 H, AC—$NH_2$), δ=6.05 (d, 1 H, Tyr—$^{\alpha}$NH—), δ=6.61 (d, 2 H, Tyr—ArH), δ=6.95 (d, 2 H, Tyr—ArH), δ=7.79 (d, 1 H, Ile—$^{\alpha}$NH), δ=8.32 (t, 1 H, Gly—$^{\alpha}$NH—), δ=9.11 (s, 1 H, Tyr—OH)

EXAMPLE 18

Synthesis of AC—Tyr—Val—OBzl

Analogously to example 16, instead of H—Leu—$NH_2$, 379.4 mg (1.0 mmol) H—Val—OBzl.pTos (Bachem Feinchemikalien AG), 175 μl buffer, 125 μl 10 M aqueous NaOH and 100 μl thermolysin suspension comprising 10 mg thermolysin (Sigma P1512) are employed.

Yield of AC—Tyr—Val—OBzl after 88 h: 230 mg (=55% of th.) $^1$H-NMR ($D_6$-DMSO, 300 MHz): δ=0.81–0.92 (m, 6 H, Val—$^{\gamma}CH_3$), δ=2.01–2.14 (m, 1 H, Val—$^{\beta}$CH—), δ=2.50–2.64 (m, 1 H, Tyr—$^{\beta}CH_2$—), δ=2.75–2.85 (m, 1 H, Tyr—$^{\beta}CH_2$—), δ=4.23 (dd, 1 H, Val—$^{\alpha}$CH—), δ=4.36–4.45 (m, 1 H, Tyr—$^{\alpha}$CH—), δ=5.13 (s, 2 H, —O—$CH_2$—), δ=5.52 (s, 2 H, AC—$NH_2$), δ=6.04 (d, 1 H, Tyr—$^{\alpha}$NH—), δ=6.62 (d, 2 H, Tyr—ArH), δ=6.96 (d, 2 H, Tyr—ArH), δ=7.30–7.40 (m, 5 H, —$C_6H_5$), δ=8.20 (d, 1 H, Val—$^{\alpha}$NH—), δ=9.13 (s, 1 H, Tyr—OH)

EXAMPLE 19

Synthesis of AC—Tyr—Phe—Ala—OBzl

Analogously to example 9a, instead of H—Ile—Ala—$NH_2$.HCl, 88 mg (0.2 mmol) H—Phe—Ala—OBzl.TFA are employed.

Yield of AC—Tyr—Phe—Ala—OBzl after 3 h: 72% of th. $^1$H-NMR;COSY($D_6$-DMSO, 300 MHz): δ=1.33 (d, 3 H, Ala—$^{\beta}CH_3$), δ=2.48–2.58 (m, 1 H, Tyr—$^{\beta}CH_2$—), δ=2.70–2.85 (m, 2 H, Tyr—$^{\beta}CH_2$—), δ=2.95–3.05 (m, 1 H, Phe—$^{\beta}CH_2$—), δ=4.14–4.24 (m, 1 H, Tyr—$^{\alpha}$CH—), δ=4.32–4.41 (m, 1 H, Ala—$^{\alpha}$CH—), δ=4.51–4.62 (m, 1 H, Phe—$^{\alpha}$CH—), δ=5.13 (s, 2 H, O—$CH_2$—), δ=5.56 (s, 2 H, AC—$NH_2$), δ=5.94 (d, 1 H, Tyr—$^{\alpha}$NH—), δ=6.60 (d, 2 H, Tyr—ArH), δ=6.90 (d, 2 H, Tyr—ArH), δ=7.14–7.28 (m, 5 H, OBzl—$C_6H_5$), δ=7.30–7.40 (m, 5 H, Phe—$C_6H_5$), δ=8.01 (d, 1 H, Phe—$^{\alpha}$NH), δ=8.46 (d, 1 H, Ala—$^{\alpha}$NH—), δ=9.12 (s, 1 H, Tyr—OH)

EXAMPLE 20

Synthesis of AC—Met—Phe—$NH_2$

Analogously to example 9a, instead of AC—Tyr—OH, 76.8 mg (0.2 mmol) AC—Met—OH [sic] 80 mg (0.4 mmol) H—Phe—$NH_2$.HCl (Degussa AG), 90 μl buffer, 50 μl 10 M aqueous NaOH and 20 μl thermolysin suspension comprising 2 mg thermolysin (Sigma P1512) are employed.

Yield of AC—Met—Phe—$NH_2$ after 3 h: 96% of th. $^1$H-NMR ($D_6$-DMSO, 300 MHz); δ=1.58–1.80 (m, 2 H, Met—$^{\beta}CH_2$—), δ=1.99 (s, 3 H, Met—S—$CH_3$), δ=2.25–2.36 (m, 2 H, Met—$^{\gamma}CH_2$—), δ=2.76–2.88 (m, 1 H, Phe—$^{\beta}CH_2$—), δ=2.98–2.08 (m, 1 H, Phe—$^{\beta}CH_2$—), δ=3.98–4.08 (m, 1 H, —$^{\alpha}$CH—), δ=4.36–4.47 (m, 1 H, —$^{\alpha}$CH—), δ=5.63 (s, 2 H, AC—$NH_2$), δ=6.23 (d, 1 H, Met—$^{\alpha}$NH—), δ=7.09 (s, 1 H. Phe—$NH_2$), δ=7.12–7.28 (m, 5 H, Phe—$C_6H_5$), δ=7.42 (s, 1 H, Phe—$NH_2$), δ=7.96 (d, 1 H, Phe—$^{\alpha}$NH—)

EXAMPLE 21

Synthesis of AC—Leu—Phe—$NH_2$

Analogously to example 20, instead of AC—Met—OH, 69.6 mg (0.4 mmol) AC—Leu—OH are employed.

Yield of AC—Leu—Phe—$NH_2$ after 70 h: 97% of th. $^1$H-NMR ($D_6$-DMSO, 300 MHz): δ=0.78–0.88 (m, 6 H, Leu—$^{\delta}CH_2$—), δ=1.16–1.35 (m, 2 H, Leu—$^{\beta}CH_2$—, Leu—$^{\gamma}$CH—), δ=1.45–1.56 (m, 1 H, Leu—$^{\beta}CH_2$—), δ=2.78–2.90 (m, 1 H, Phe—$^{\beta}CH_2$—), δ=2.99–3.08 (m, 1 H, Phe—$^{\beta}CH_2$—), δ=3.90–4.00 (m, 1 H, —$^{\alpha}$CH—), δ=4.36–4.45 (m, 1 H, —$^{\alpha}$CH—), δ=5.58 (s, 2 H, AC—$NH_2$), δ=6.08 (d, 1 H, Leu—$^{\alpha}$NH—), δ=7.06 (s, 1 H, Phe—$NH_2$), δ=7.12–7.28 (m, 5 H, Phe—$C_6H_5$), δ=7.34 (s, 1 H, Phe—$NH_2$), δ=7.82 (d, 1 H, Phe—$^{\alpha}$NH—)

EXAMPLE 22

Removal of the carbamoyl protective group by splitting off (by the example of carbamoyl-aspartam as an example) by means of the enzyme technique 16 ml (65.6 U) carbamoylase and 50.6 mg thermolysin are initially introduced together into water and are stirred overnight (approx. 18 h). Carbamoyl-aspartam (470 mg) [sic], 1.25 mmol) is added. Total volume: ≈16 ml. The pH is between 6.5 and 7.0. After 24 h, carbamoyl-aspartam is no longer detectable. According to HPLC calibration, the conversion to aspartam is 98.3%.

EXAMPLE 23

Removal of the carbamoyl protective group by splitting off (by the example of carbamoyl-L-aspartam by way of example) by addition of sodium nitrite 4.72 g (12.6 mmol) carbamoyl-L-aspartam potassium salt are initially introduced into 60 ml $H_2O$/40 ml HCl (conc., technical grade), the mixture is cooled to 5° C. (pH=0.80) and 15.1 ml (15.1 mmol) $NaNO_2$ solution are slowly metered in (1 ml/10 min). The mixture is allowed to after-react for approx. 1 h, before the reaction mixture is neutralized with 50 wt. % sodium hydroxide solution. The reaction mixture is left overnight at RT, before the precipitate which has separated out is separated off and discarded. The mother liquor is then concentrated until aspartam precipitates out. The aspartam thus obtained is dried to constant weight in vacuo at 60° C. The reaction proceeds quantitatively.

What is claimed is:

1. Process for the preparation of peptides of the structure I,

I wherein $R^1$ and $R^2$ independently of one another denote hydrogen, ($C_1$–$C_6$ $Q_n$) alkyl, where n=0–5 and wherein Q is a mono or poly substituent on a carbon and a member of the group consisting of heteroatoms of the group consisting of N, O and S, said heteroatoms being unsubstituted or mono or poly substituted wherein the substituent is a member of the group consisting of hydrogen, (C1–C4) alkyl and benzyl, or being bonded to said ($C_1C_6$) alkyl group via a double bond, unsubstituted or mono or Poly substituted phenyl or benzyl, wherein the substituent is a member of the group consisting of halogen or hydroxyl and heteroaralkyl, $R^3$ denotes ($C_1$–$C_4$) alkoxy, $NH_2$, hydroxyl, $NR^1$ $R^2$, unsubstituted or mono or Poly substituted benzyloxy, wherein the substituent is a member of the group-consisting of halogen, nitro, $NH_2$ ($C_1$–$C_4$),alkyl, ($C_1$–$C_4$) and one or more units of the formula II

II

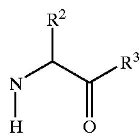

wherein compounds of formula III or a salt form thereof,

III

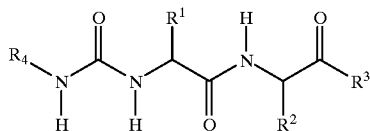

wherein $R^1$, $R^2$ and $R^3$ have the above-mentioned meaning and $R^4$ denotes hydrogen are reacted with a carbamoylase to remove the carbamoyl protective group.

2. Process for the preparation of peptides of the general structure III,

III

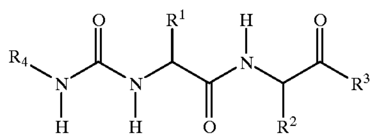

as defined in claim 1 wherein a compound of the type IV or a salt form of IV, in which $R^1$ and $R^4$ have the abovementioned meaning,

IV

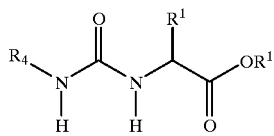

is reacted with a compound of the type V or an acid addition salt thereof, wherein $R^1$ and $R^3$ have the abovementioned meaning

V

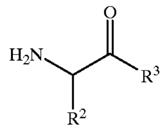

in the presence of hydrolases.

3. Process according to claim 1, wherein the reaction with carbamoylase is carried out in a temperature range between 10° C. and 50° C.

4. Process according to claim 1, wherein the reaction with carbamoylase is carried out in a pH range between 5 and 11.

5. Process according to claim 1, wherein the carbamoylase originates from the microorganisms DSM 7329, DSM 7330 or DSM 9771.

6. Process according to claim 1, wherein the carbamoylase is employed in a partly purified or purified, isolated or immobilized state.

7. Process according to claim 3, wherein the reaction takes place in an aqueous medium.

8. Process according to claim 1, wherein the peptide derivative cleaved is aspartame.

9. Process according to claim 2, wherein the peptide coupling is carried out in a dense suspension.

10. Process according to claim 9, wherein the substrate and product are partially dissolved and partially precipitated.

11. Process according to claim 3 wherein the reaction is carried out between 20° C. and 35° C.

12. Process according to claim 11 wherein the reaction is carried out between 25° C. and 30° C.

13. Process according to claim 4 wherein the reaction is carried out at pH between 6.5 and 8.

14. Process according to claim 2, wherein the reaction takes place in the presence of a solvent.

15. Process according to claim 14, wherein the reaction takes place in the presence of a base.

16. Process for the formation of a compound of type III structure having the formula $AC[Q^1][Q^2]$ wherein $Q^1$ is Asp, Asp.Phe or Tyr, and $Q^2$ is Phe.OMe
Phe.$NH_2$
Leu.$NH_2$
Ile.Gly.OMe
Ile.Ala.$NH_2$
Val.$NH_2$
Met.$NH_2$
Nvl.$NH_2$, which comprises reacting a compound of type IV structure selected from the group consisting of:

AC.Asp(OK)(OK), AC.Asp.Phe.OMe, AC. Tyr.OH, AC.Met.OH and Ac.Leu.OH, with a compound of type V structure selected from the group consisting of H.Phe.OMe.HCl
H.Phe.$NH_2$.HCl
H.Leu.$NH_2$
H.Ile.Gly.OMe.HCl H.Ile.Ala.$NH_2$.HCl
H.Val.$NH_2$.HCl
H.Met.$NH_2$.HCl
H.Nvl.$NH_2$.HCl
H.Ile.$NH_2$.HCl
H.Val.OBzl.p.Tos, and
H.Phe.Ala.OBzl.TFA, in the presence of a hydrolase wherein AC is carbamoyl, K is potassium, Bzl is benzyl, P.Tos is p-tosylate and TFA is trifluoroacetyl.

17. Process according to claim 16 wherein the reaction is carried out in the presence of a solvent.

18. Process in accordance with claim 17 wherein the reaction is carried out in the presence of a base.

19. Process for the synthesis of a compound of type I structure having the formula $$[Q^1][Q^2]$$

which comprises treating a compound of type III structure having the formula $$AC[Q^1][Q^2]$$

as defined in claim 16 with a carbamoylase.

* * * * *